United States Patent [19]

Brinton

[11] Patent Number: 4,769,240

[45] Date of Patent: Sep. 6, 1988

[54] PILI OF NEISSERIA AND VACCINE COMPOSITIONS CONTAINING SAME

[75] Inventor: Charles C. Brinton, Pittsburgh, Pa.

[73] Assignee: BACTEX, Inc., Pittsburgh, Pa.

[21] Appl. No.: 543,087

[22] Filed: Nov. 17, 1983

Related U.S. Application Data

[63] Continuation of Ser. No. 413,536, Aug. 31, 1982, abandoned, which is a continuation of Ser. No. 187,049, Sep. 15, 1980, abandoned.

[51] Int. Cl.$^4$ ................... A61K 39/02; A61K 39/095
[52] U.S. Cl. ........................... 424/92; 424/85; 424/87; 424/88; 436/511
[58] Field of Search .............. 424/85, 87, 88; 436/511, 543; 435/871; 260/112 R; 530/825

[56] References Cited

U.S. PATENT DOCUMENTS

| | | | |
|---|---|---|---|
| 4,203,971 | 5/1980 | Buchanan | 424/92 |
| 4,461,838 | 7/1984 | Brinton et al. | 436/511 |
| 4,601,903 | 7/1986 | Frasch | 424/92 |
| 4,696,896 | 9/1987 | Brinton et al. | 424/92 X |

OTHER PUBLICATIONS

Buchanan et al., J. Infect. Dis., 136, Supplement, Aug. 1977: S132–S137.
Tramont et al., J. Infections Diseases, v. 130, No. 3, 240–247, Sep. 1974.
Devoe et al., Infection and Immunity, vol. 10, 872–876, Oct. 1974.

*Primary Examiner*—Sidney Marantz
*Attorney, Agent, or Firm*—Omri M. Behr

[57] ABSTRACT

It has been found that immunologically related piliated organisms exhibit a hierarchic relationship wherein the cross-reactivity of the antisera to first pili against second pill in the series is greater for the senior members of the series than the cross-reactivity of the first pili with the corresponding antisera from second pili. This asymmetric relationship leads to the situation where the juniormost pili in the series may be utilized to detect the presence of all members of the family senior to it and conversely the seniormost pili may be utilized to protect against infection by all strains junior in the series.

8 Claims, No Drawings

PILI OF NEISSERIA AND VACCINE COMPOSITIONS CONTAINING SAME

RELATED APPLICATIONS

This application is a continuation of application Ser. No. 413,536, filed 8/31/82, now abandoned, which in turn was a continuation of Ser. No. 187,049, filed 9/15/80, now abandoned.

BACKGROUND OF THE INVENTION

The presence of pili on certain organisms was noted many years ago and the first isolation of such material was reported in 1959 by Brinton in Nature 183, 782–786. Since that time many piliated organisms have been identified. Among these may be mentioned:

Neisseria gonorrhoeae
Escherichia coli
Pseudomonas aeruginosa
Neisseria meningitidis, lactamica
Proteus vulgaris
Moraxella species
Vibrio cholerae
Salmonella species
Bordatella pertussis
Falvobacterium species
Klebsiella species
Serratia species
Enterobacter species
Corynebacterium diphtheriae
Corynebacterium renale
Actineobacter species
Flavobacterium species
Aeromonas species
Shigella flexneri The pili of these various organisms may be separated from the cells and from cell debris and provide pilic material which, when injected into an immune-responsive system, will cause the formation of antibodies to said pilic material.

Heretofore, the immunological relationship of members of a particular group of immunologically cross-reactive piliated organisms has been unclear. There have been reasons to suppose that the existence of a common antigenic factor as well as the existence of individual determinants or groups of determinants specific to each particular strain. Heretofore, the nature of this relationship has not been specified.

SUMMARY OF THE INVENTION

It has been found that a well definable hierarchial relationship can be provided between all members of the group of the immunologically cross-reactive piliated organisms, that is to say, where organisms are piliated and the pili thereof may be isolated and purified and utilized to form antisera containing antibodies to said pili, the organisms may be arranged in a hierarchial order. It has been the surprising finding of the present work that within such an immunologically cross-reactive group the degree of cross-reactivity between the antiserum of a first strain and the pili of a second strain in the group will not be the same as the degree of cross-reactivity between the antiserum to the pili of said second strain with the pili causing the antibodies to said first strain.

This surprising difference has led to a mode of ranking members of an immunological group in a clearly defined hierarchy.

In carrying out this method, pili of the group of piliated organisms are prepared free of cell material and cell debris. The pili are then provided to an immune responsive system, such as, for example, mice or rabbits, and the antisera to said pili containing the antibodies to said pili are then isolated in the usual manner.

Cross-reaction experiments of the type well known to the art, for example, ELISA Tests, are carried out between the pili and the antisera. Suitably, these results are translated on a table in matrix form showing the antisera on the columns and the corresponding pili on the rows. Such a classification will provide the homologous reaction readings between a particular pilus and the antiserum corresponding thereto upon the diagonal. The diagonal numbers are then normalized to the same predetermined value and the corresponding titers for all heterologous pili against each antiserum adjusted accordingly. The resultant Table will indicate the hierarchial relationship.

Upon rearrangement of this normalized Table, in the order of seniority, it will be seen that a remarkable but consistent asymmetry exists between the titers of the antisera with the pili. The titers obtained between the antiserum to the pili of a more senior strain and the pili of a more junior strain is always greater than the titer obtained between the pili of the said more senior strain with the antiserum to the pili of the said more junior strain. This relationship holds within families of immunologically related pili.

This remarkable result has led to the conclusion that within any such group the senior organisms contain an immunological factor which will provide an immune response against all organisms in the hierarchy equal in rank or junior to it, thus providing a vaccine inducing protection against infection therefrom. Conversely, the juniormost organisms will contain a factor common to all organisms senior to them in the hierarchy, thus enabling the juniormost organism to be utilized for the purpose of detecting antibodies to members of the family senior thereto.

EXPERIMENTAL

EXAMPLE I

Method of Growth of Organisms—General

The meningococci were routinely propagated on GC agar base medium (Difco) plus 10% DSF (defined supplement with iron, a solution of 31% glucose, 0.78% L(+)-glutamine, and 0.039% ferric nitrate) and $1.5 \times 10^{-5}$% thiamine pyrophosphate (Brinton et al., 1978).

When the meningococci were grown for pilus production, the organisms were seeded on the supplemented GC agar medium described above omitting the thiamine pyrophosphate. About 500 ml of medium were poured into a sterile 39 cm×26 cm×2.3 cm aluminum tray with a sterile aluminum lid. Inoculum for the tray was prepared by suspending a 20 to 24 hour growth of a desired meningococcal colony type from a petri dish in 0.7% casamino acid (Difco) and 0.02% thiamine pyrophosphate and spreading it over the GC agar surface with a long handled glass spreader at a cell density of about $10^9$ cells per tray. The petri dish was inoculated with 5 to 10 colonies of the desired colony types in each of the four quadrants. Both the inoculum and production plates were incubated for 20 to 24 hours at 35° C. in a 80% humidity-5% carbon dioxide incubator (Forma Scientific Co.).

EXAMPLE II

Pilus Purification

The meningococci were grown as described above. After approximately 20 to 24 hours incubation, they were harvested and processed. The exact procedures were strain dependent and there was no general pilus pilus purification method that might apply to all meningococci. However, all the purification methods described below made use of the strong tendency of pilus rods to form longitudinal aggregates (paracrystals, Brinton, 1965) under some solvent conditions and the dissociation of the aggregates under another set of conditions.

(a) *N. meningitidis* ATCC 13090

The meningococci were harvested by washing the agar surface with a small volume of Tris.HCl buffered saline 0.05M, pH 9.0. The suspended growth was then aspirated into a vacuum flask. The growth from all trays was pooled. After the suspensions were blended at 4000 rpm in small aliquots of 200 ml for 2 minutes in the 450 ml cup of the Sorvall omnimixer, the cells were removed by centrifugation at 13,000 g for 30 minutes. The supernatant was then further clarified at 23,000 g for an hour while the cell pellet from the previous centrifugation step was reextracted. The two supernatants were combined and dialyzed against two changes of 15×volume of 0.1M phosphate buffer at pH 6,8. The crystallization of pilus aggregates was evident by the appearance of streaming birefringence inside the dialysis sac when it was swirled. The aggregates were removed by centrifugation at 13,000 g for an hour and the supernatant was discarded. The pellet was resuspended by magnetic stirring for about 45 minutes in a minimal volume of Tris.HCl buffered saline such that very few or no crystals were observed at 320×magnification under a Leitz darkfield microscope. The solution was then clarified at 23,000 g for an hour. The pellet was discarded and the supernatant was dialyzed against 0.1M phosphate buffer at pH 9.0. Usually three to four cycles of solubilization and crystallization were sufficient to achieve a reasonably pure preparation as judged by SDS-PAGE. The purified pilus crystals were stored in the aggregated state in 0.02% sodium azide.

(b) *N. meningitidis* NRC 1597

The harvesting procedure, the speed and duration of blending and centrifugation were the same as in the purification method described for ATCC 13090. The modifications were as follows: harvesting buffer, 0.02M phosphate buffered saline at pH 6.8; crystallization conditions, addition of 4M stock $MgCl_2$ to 0.1M $Mg^{++}$; solubilization buffer, 0.03M phosphate buffered saline at pH 6.8.

(c) *N. meningitidis* NRC 1667

The cells were grown and harvested in phosphate buffered saline at pH 6.8. The suspension was then blended at 4000 rpm for 2 minutes in 200 ml aliquots. The supernatant from a 13,000 g×30 minute spin was further clarified by centrifuging at 23,000 g for an hour. Solid sodium dextran sulfate 2000 (Pharmacia) was added to the solution to a final concentration of 1%. After standing for 1 hour at 4° C., 0.15 ml of 3M stock KCl per ml of solution was added to precipitate the dextran sulfate. This cloudy suspension was then clarified by a low speed centrifugation (2000 g for 15 minutes) and a high speed centrifugation (23,000 g for 1 hour). The resulting supernatant was adjusted to 5% concentration of PEG-6000. Crystals appeared immediately but the process of crystallization was allowed to proceed for several hours. The crystals were then collected at 13,000 g for 1 hour, redissolved ina minimal amount of solvent buffer and clarified at 23,000 g for an hour. After two cycles, the preparation was quite pure as judged by SDS-PAGE. However, UV absorption spectroscopy showed the presence of nucleic acids. To remove nucleic acid contaminants, a preparative CsCl density gradient equilibrium centrifugation was performed. At the end of the run, fractions were collected by puncturing the bottom of the centrifuge tube. Fractions around the protein peak at density of 1.32 gm/cc were pooled, dialyzed against several changed of phosphate buffered saline, pH 6.8, and finally recrystallized at 3% PEG concentration. The purified pili were stored in 0.02% sodium azide, phosphate buffered saline at pH 6.8.

Subsequent studies indicated preliminary fractionation by sodium dextran might be omitted if the solution were adjusted to 0.5M sodium chloride prior to crystallization.

(d) *N. meningitidis* NRC 1700

The harvesting, blending and centrifugation procedures were the general steps described for preparation of ATCC 13090 and NRC 1597 meningococcal pili. The buffer systems were like that of the gonococcal pilus preparation method. The harvesting and solubilizing buffer was 0.63M monoethanolamine hydrochloride at pH 10.5. The crystallization buffer contained 10% saturated ammonium sulfate and 1.7% PEG-6000.

EXAMPLE III

Density Gradient Equilibrium Centrifugation

Two kinds of CsCl density centrifugation were used in this study: the analytical and the preparative methods.

To determine the buoyant density of a pilus protein, the analytical procedure was followed. About 0.7 mg of pilus protein was dissolved in Tris-HCl buffered saline at pH 9.0; solid CsCl was added to the solution such that the average solution density was about 1.3 gm per ml. The solution was then centrifuged in a SW 41 Ti rotor at 35,000 rpm for 40 hours at 4° C. At the end of the run, the bottom of the centrifuge tubes was punctured and fractions were collected dropwise. Refractive index was determined at room temperature using a Zeiss Abbe refractometer, and the protein content of each fraction was determined either by a protein-dye binding assay or by its absorbance at 280 nm. The density of the protein peak at 4° C. was estimated from a refractive index—CsCl density conversion table constructed from data available in the International Critical Tables (Vol. 3, page 94, 1928).

EXAMPLE IV

Preparation Density Gradient Equilibrium

Preparative CsCl density centrifugation was used as an intermediate step in the purification of NRC 1667 meningococcal pili. Preformed gradient of six steps of CsCl was employed. Each step contained 3.0 ml of CsCl and the density ranged from 1.18 gm/cc to 1.28 gm/cc (1.18, 1.20, 1.22, 1.24, 1.26, 1.28). Up to 19 ml of partially purified pilus solution could be accommodated per centrifuge tube. The solution was spun at 22,000 rpm for 40 hours in a SW 27 rotor at 4° C. Collection and assay of the fractions were described as in the analytical centrifugation method.

EXAMPLE V

Preparation of the Antigens and the Antisera

To ensure that pure pili were used in the preparation of antisera, the purified meningococcal pili were subjected to a final purification step of CsCl density gradient centrifugation. This highly purified preparation was then injected subcutaneously in the dorsal area of the neck of a pre-bled 3 to 5 pound New Zealand white rabbit. The rabbit received approximately 300 to 5000 ug of pilus protein in a 1:1 suspension of pili and Freund's incomplete adjuvant (Difco). The injection was to be repeated three times at approximately 10 day intervals. At the end of the injection schedule, the animal was bled from the ear.

Blood was drawn from the central artery of the rabbit ear without the use of any anesthetics on the animal. The hair on the back of the ear was shaved off and the artery was temporarily distended by rubbing the skin with xylene. Blood was collected into a sterile syringe fitted with a 25 guage needle. Ten to twenty ml of blood could be obtained this way.

Blood was then transferred to a sterile centrifuge tube and allowed to clot at room temperature for 30 minutes. After breaking up the clot and freeing it from the vessel wall, the entire specimen was refrigerated overnight at 4° C. The tube was then spun at 4000 g for 30 minutes; and the serum removed and saved.

This antiserum preparation was distributed in small aliquots, frozen in liquid nitrogen and stored at −20° C.

EXAMPLE VI

Enzyme Linked Immunosorbent Assay

Description of this assay and the interpretation of the results were discussed in detail by Brinton et al. (1978). The first antibody was obtained from rabbits immunized with purified pili. The second antibody was goat anti-rabbit IgG (light and heavy chains) conjugated with horseradish peroxidase (Cappel Inc.). When human sera were assayed, goat anti-human IgG conjugte was used.

Serum titers were calculated from the absorbance and the dilution factor, and finally standardized by comparison with serum controls. The standard curve was a plot of absorbance vs relative serum concentration obtained by reacting a serum standard at several dilutions with its homologous antigen. Absorbances between 0.1 and 1.0 were used for calculations. Titers reported were geometric means of two runs. Inclusion of standards in every assay series eliminated titer fluctuations due to variations in the test reagents.

Calculation of Rabbit Serum Titers

The ELISA titers of rabbit sera were calculated from a standard curve which was based on the reaction of a standard rabbit serum (anti-GC 3-2) at several dilutions with its homologous antigen (GC 3-2 pili). This serum was arbitrarily set to have a titer of 10.000.

Titers of unknown sera were determined from the linear regression line of the serum standard. These titers when multiplied by the dilution factor gave the titers of undiluted sera.

EXAMPLE VII

Immunological Characterization of Meningococcal Pili

1. Antigenicity of Meningococcal Pili

When rabbits were hyperimmunized with the pilus antigens, elevated levels of specific antibodies were found in the antisera using the enzyme-linked immunosorbent assays (Table 1).

TABLE 1 a: Homologous and heterologous titers of rabbit anti-meningococcal sera

| Pili | Antisera | | | | |
|---|---|---|---|---|---|
| | ATCC 13090 | NRC 1597 | NRC 1667 | NRC 1700 | pooled normal |
| ATCC 13090 | 3005 | 691 | 135 | 53 | 7 |
| NRC 1597 | 115 | 2360 | 329 | 82 | 7 |
| NRC 1667 | 784 | 147 | 838 | 67 | 5 |
| NRC 1700 | 560 | 603 | 210 | 407 | 12 | b: Normalized titers

| Pili | Antisera | | | |
|---|---|---|---|---|
| | ATCC 13090 | NRC 1597 | NRC 1667 | NRC 1700 |
| ATCC 13090 | 100 | 29 | 17 | 13 |
| NRC 1597 | 4 | 100 | 40 | 20 |
| NRC 1667 | 26 | 6 | 100 | 17 |
| NRC 1700 | 19 | 26 | 25 | 100 |

Average heterologous titer = 20.1 ± 2.9

2. Cross-reactivities among Meningococcal Pili

Table 1a shows the homologous and heterologous ELISA titers of anti-pilus sera prepared in hyperimmunized rabbits against purified meningococcal pili. Considerable cross-reactivity was observed. Average cross-reactivity among the four meningococcal pili was about 20.1±2.9 (Table 2b). Asymmetric cross-reactivity was observed for the meningococcal pili.

3. Cross-reactivity with Other Somatic Pili

Hyperimmune rabbit anti-meningococcal pilus sera and antisera directed against other kinds of somatic pili were tested for cross-reactivity. Table 2a shows the normalized homologous and heterologous ELISA titers of antisera prepared in rabbits against four meningococcal and four gonococcal.

Among the three kinds of somatic pili examined here, gonococcal and meningococcal pili were found to have cross-reacting antibodies.

Average cross-reactivity of pili within the species of the meningococcus and gonococcus are 12.8±2,4% and 20.1±2.9%, respectively. Asymmetric cross-reactivities between meningococcal and gonococcal pili were also observed (grouped data, Table 2b). The average normalized hererologous titers of the gonococcal pilus antisera for meningococcal pili was about 5.5±1.1%; while the average heterologous titer of antimeningococcal pilus sera was about 16.9±2.3%.

TABLE 2 a: Normalized homologous and heterologous titers of rabbit antisera against purified pili

| Pili | Antisera | | | | | | | |
|---|---|---|---|---|---|---|---|---|
| | N. gonorrhoeae | | | | N. meningitidis | | | |
| | 3-2 | M-2 | Nor-2 | C-2 | 13090 | 1597 | 1667 | 1700 |
| GC | | | | | | | | |
| 3-2 | 100 | 10 | 7 | 16 | 5 | 28 | 16 | 17 |
| M-2 | 10 | 100 | 3 | 11 | 3 | 35 | 17 | 24 |
| Nor-2 | 33 | 16 | 100 | 20 | 3 | 25 | 14 | 19 |
| C-2 | 16 | 9 | 2 | 100 | 7 | 26 | 18 | 14 |
| MC | | | | | | | | |
| 13090 | 8 | 3 | 2 | 7 | 100 | 29 | 17 | 13 |

TABLE 2-continued

| 1597 | 8 | 7 | 1 | 7 | 4 | 100 | 40 | 20 |
| 1667 | 1 | 1 | 1 | 5 | 26 | 6 | 100 | 17 |
| 1700 | 8 | 15 | 2 | 12 | 19 | 26 | 25 | 100 | b: Average cross-reactivities* between *N. gonorrhoeae*, *N. meningitidis* and *E. coli* somatic pili

| | Antisera | | |
|---|---|---|---|
| Pili | *N. gonorrhoeae* | *N. meningitidis* | *E. coli* |
| *N. gonorrhoeae* | 12.8 ± 2.4 | 16.9 ± 2.3 | 1.3 ± 0.3 |
| *N. meningitidis* | 5.5 ± 1.1 | 20.1 ± 2.9 | 1.5 ± 0.9 |

Grouped data from Table 17a
*average heterologous titers

4. Cross-absorption Experiments

Exhaustive absorption experiments confirmed that pili of *N. meningitidis* and *N. gonorrhoeae* share common antigenic determinants. Table 3a shows ELISA titers of the pilus antisera absorbed with a heterologous meningococcal pilus and Table 3b shows the titers of the same set of antisera absorbed with a gonococcal pilus. Absorptions of the antipilus antisera with heterologous neisserial pili significantly reduced the magnitude of the heterologous titers.

TABLE 3 a: Normalized homologous and heterologous titers of antisera absorbed with NRC 1597 meningococcal pili

| | Antisera | | | | | | |
|---|---|---|---|---|---|---|---|
| | *N. gonorrhoeae* | | | | *N. meningitidis* | | |
| Pili | 3-2 | M-2 | Nor-2 | C-2 | 13090 | 1667 | 1700 |
| GC 3-2 | 100 | 2 | 6 | 3 | 2 | 6 | 8 |
| M-2 | 1 | 100 | 1 | 1 | 1 | 2 | 15 |
| Nor-2 | 26 | 8 | 100 | 7 | 0 | 3 | 3 |
| C-2 | 1 | 5 | 0 | 100 | 3 | 1 | 1 |
| MC 13090 | 1 | 0 | 0 | 0 | 100 | 2 | 6 |
| 1597 | 0 | 0 | 0 | 0 | 0 | 1 | 3 |
| 1667 | 0 | 0 | 0 | 0 | 23 | 100 | 6 |
| 1700 | 0 | 9 | 0 | 0 | 13 | 6 | 100 | b: Normalized homologous and heterologous titers of antisera absorbed with M-2 gonococcal pili

| | Antisera | | | | | | |
|---|---|---|---|---|---|---|---|
| | *N. gonorrhoeae* | | | | *N. meningtidis* | | |
| Pili | 3-2 | Nor-2 | C-2 | 13090 | 1597 | 1667 | 1700 |
| GC 3-2 | 100 | 6 | 1 | 1 | 0 | 2 | 4 |
| M-2 | 0 | 0 | 0 | 0 | 8 | 1 | 6 |
| Nor-2 | 19 | 100 | 3 | 0 | 1 | 4 | 3 |
| C-2 | 1 | 0 | 100 | 3 | 5 | 6 | 7 |
| MC 13090 | 0 | 0 | 0 | 100 | 7 | 4 | 7 |
| 1597 | 0 | 0 | 1 | 1 | 100 | 25 | 12 |
| 1667 | 0 | 0 | 1 | 22 | 0 | 100 | 14 |
| 1700 | 0 | 0 | 0 | 14 | 3 | 12 | 100 |

EXAMPLE IX

The final preparation of the pilus vaccine may be exemplified by the preparation of pilus vaccine from *N. meningitidis* 1597. The recrystallized pili are dialyzed against phosphate-buffered saline pH 6.8, ionic strength 0.15 in which buffer the pilus crystals are solubilized. The vaccine is sterilized by filtration through 0.45 micron pure site membrane filters. The pili thus prepared are of quality sufficient to pass the standards of the Bureau of Biologics, Food and Drug Administration, for general safety, sterility and potency.

The vaccine is administered parenterally by subcutaneous or intramuscular injection. Since the pili are solid, any pharmaceutically acceptable suspending medium may be employed. The concentration of pili in the vehicle is not critical. The sole criterion of desirability being that the pili shall be sufficiently finely divided to provide a suspension which meets generally accepted standards of syringeability. A concentration of 0.1 to 2.0, preferably about 1.0 mg of pilus protein per ml, of suspending medium is especially suitable.

It is generally preferred to administer the vaccine composition in more than one dose separated by a predetermined time factor. This time factor is selected to permit the formation of an adequate titer of antibodies to the pili in the injected subject.

Since there are no local or systemic toxic effects engendered by the injection of vaccine, there appear to be no upper limits to the dosage administered. It has been found suitable, however, to administer between 1 and 1000 micrograms of pili per kilogram of body weight suitably about 60 micrograms of body weight in each injection.

Utilizing the procedures disclosed above, pili derived from *N. meningitidis* and *N. lactamica*, in particular *N. meningitidis*, are utilized to protect against against infection of vertebrate subjects not only against homologous, i.e., *N. meningitidis* infection but also against *N. gonorrhoeae* infection.

TABLE 4

ASSIGNMENT OF SENIORITY

| Strain | rank by pili[a] | rank by serum[a] | combined rank[b] |
|---|---|---|---|
| MC 13090 | 6 | 3 | 4 |
| 1597 | 7 | 8 | 8 |
| 1667 | 8 | 7 | 8 |
| 1700 | 3 | 6 | 4 |
| GC 3-2 | 2 | 4 | 3 |
| C-2 | 5 | 5 | 5 |
| M-2 | 4 | 2 | 3 |
| Nor-2 | 1 | 1 | 1 | data from table 1 a
[a]ranking method by A. Labik and C. Brinton
rank by pili
(i) determine the average heterologous titer for each pili
(ii) rank the pili based on the average titers. The most junior pili has the highest titer (rank #1).
rank by serum
(i) determine the average heterologous titer for each serum.
(ii) rank the serum based on the average titer. The antiserum to the most junior antigen has the lowest titer (rank #1).
[b]combined rank = geometric mean of the two ranks.

TABLE 5

AMINO ACID COMPOSITION OF MENINGOCOCCAL PILI

| Amino Acid | ATCC 13090 | NRC 1597 | NRC 1667 | NRC 1700 |
|---|---|---|---|---|
| AsX | 23 | 26 | 17 | 28 |
| Thr | 15 | 18 | 18 | 10 |
| Ser | 20 | 17 | 18 | 22 |
| GlX | 18 | 21 | 13 | 18 |
| Pro | 6 | 6 | 4 | 5 |
| Gly | 14 | 15 | 15 | 16 |
| Ala | 34 | 26 | 23 | 38 |
| Cys(½) | 2 | 2 | 2 | 3 |
| Val | 16 | 14 | 11 | 15 |
| Met | 2 | 2 | 4 | 2 |
| Ile | 8 | 10 | 8 | 9 |
| Leu | 10 | 12 | 9 | 11 |
| Tyr | 6 | 7 | 6 | 7 |
| Phe | 1 | 2 | 5 | 1 |
| His | 3 | 3 | 2 | 3 |
| Lys | 14 | 13 | 13 | 16 |
| Arg | 5 | 6 | 3 | 6 |
| Trp | 4 | 4 | 2 | 5 |

TABLE 6

BUFFER AND STOCK SOLUTIONS

Buffers
TBS: 0.05 M Tris(hydroxymethylaminomethane) hydrochloride buffered saline

TABLE 6-continued
BUFFER AND STOCK SOLUTIONS

```
              8.5 gm NaCl (Fisher)
              6.0 gm Tris (Sigma 7-9)
              add water to one liter
              adjust pH to 9.0 with concentrated HCl (Fisher)
PBS:          0.02 M sodium phosphate buffered saline at pH 6.8
              1.4 gm sodium dihydrogen phosphate (Fisher)
              1.4 gm disodium hydrogen phosphate (Fisher)
              6.4 gm NaCl
              add water to one liter
PB:           0.1 M sodium phosphate buffer at pH 6.8
              7.1 gm sodium dihydrogen phosphate
              6.9 gm disodium hydrogen phosphate
              add water to one liter
EAB:          0.63 M monoethanolamine hydrochloride buffer at
              pH 10.5
              37.5 ml monoethanolamine (Fisher)
              957 ml water
              6.3 ml concentrated HCl
Stocks
KCL:          3 M potassium chloride
              223.7 gm KCl (Fisher)
              add water to one liter
PEG:          30% (W/W) polyethylene glycol
              30 gm PEG-6000 (Carbowax)
              70 gm water
              dissolve by stirring and filter through 0.45 um Millipore
              filter
MgCl2:        4 M magnesium chloride
              381 gm MgCl2 (Fisher)
              add water to one liter
              filter through 0.45 um Millipore filter
SAS:          saturated ammonium sulfate at pH 10.5
              760 gm ammonium sulfate (Baker)
              1000 ml 0.63 M EAB at pH 10.5
              adjust pH to 10.5 before use
```

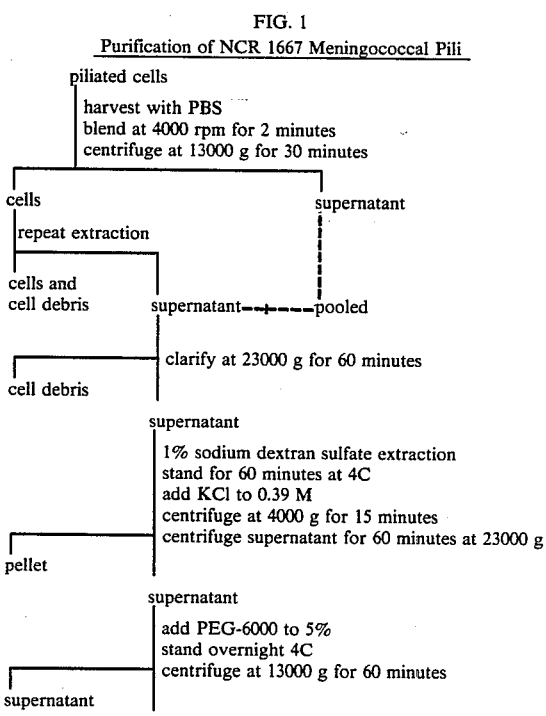

FIG. 1
Purification of NCR 1667 Meningococcal Pili

```
pellet
   │
   ├ redissolve in PBS
   │ clarify at 23000 g for 60 minutes
   │ repeat crystallization with PEG
   │ final preparative CsCl step gradient
   │    centrifugation
   │ dialysis in PBS and recrystallization
   │
Purified pili preparation
   stored in PBS with PEG and sodium azide (0.02%)
```

I claim:

1. A method of determining the presence of antibodies to pili derived from piliated organisms in an immunologically related hierarchic group of piliated organisms, the antisera against pili of strains in said group cross-reacting immunologically with pili of strains of all members of said group which comprises:
   (a) providing the pili of individual strains of organisms comprising said group, said pili being substantially free of non-pilic cell material and cell debris,
   (b) providing said pili to an immune responsive system to generate antisera to said pili,
   (c) isolating said antisera,
   (d) reacting each of the aforesaid pili with each of the thus obtained antisera and measuring the degree of cross-reactivity between said pili and said antisera,
   (e) normalizing the degree of cross-reactivity of (d) to designate a common value for all homologous pilus/antiserum reactions,
   (f) arranging said strains in order of reactivity of antisera with pili in said group to provide that the titer of antisera agaist pili from a more senior strain reacting with a pili of a more junior strain is greater than the titer of the antisera against pili from said more junior strain reacting with pili from said more senior strain, whereby the hierarachy of the group may be determined,
   (g) determining the identity of the juniormost strain of the group in accordance with the foregoing procedures,
   (h) reacting the pili derived from said junior strain with antisera suspected of containing antibodies against pili of piliated organisms belonging to said herarachial group whereby an immunological cross-reaction between said antisera and said pili indicates the presence of antibodies at least to pili in said antisera equivalent or senior in said hierarachy to pili of said junior strain.

2. A vaccine composition effective against infections by organisms selected from the group comprising N. meningitidis, and N. gonorrhoeae, which comprises substantially pure pili, substantially free of non-pilic cell material and cell debris derived from N. meningitidis ATCC 13,090, NRC 1597, NRC 1667 or NRC 1700.

3. A method of immunizing a vertebrate subject against infections by organisms selected from the group comprising N. meningitidis and N. gonorrhoeae, which comprises administering to said subject an effective amount of substantially pure pili, substantially free of non-pilic cell material and cell debris derived from N. meningitidis ATCC 13090, NRC 1597, NRC 1667 or NRC 1700.

4. A method of immunizing vertebrate subject against infection by organisms of N. gonorrhoeae which comprises administering to said subject an effective amount of substantially pure pili, substantially free of non-pilio cell material and cell debris derived from *N. meningitidis* ATCC 13090, NRC 1597, NRC 1667 or NRC 1700.

5. A vaccine for protecting a subject against infection caused by piliated *N. meningitidis* organisms which comprises a pharmaceutically acceptable carrier and whole *N. meningitidis* pili designated vaccine pili, previously separated from other *N. meningitidis* organism components, in an amount capable of raising the antibody level of the subject to a level sufficient to provide such protection, the whole cells of said piliated organisms from which the vaccine pili are derived as well the whole cells of the infection causing organisms, being agglutinable by antisera derived from pili of at least one of the following strains:

ATCC 13090, NRC 1597, NRC 1667 and NRC 1700.

6. A vaccine of claim 5, comprising pili derived from more than one member of the designated group of strains.

7. A method of protecting a subject against infection caused by piliated *N. meningitidis* organisms which comprises administering to said subject whole *N. meningitidis* pili designated vaccine pili, previously separated from other *N. meningitidis* organism components, in an amount capable of raising the antibody level of the subject to a level sufficient to provide such protection, the whole cells of said piliated organisms from which the vaccine pili are derived as well the whole cells of the infection causing organisms being agglutinable by antisera derived from pili of at least one of the following strains:

ATCC 13090, NRC 1597, NRC 1667 and NRC 1700.

8. A method of claim 7, comprising administering to said subject pili derived from more than one member of the designated group of strains.

* * * * *